(12) United States Patent
Tropello (10) Patent No.: US 10,219,778 B2
(45) Date of Patent: Mar. 5, 2019

(54) COAPTATION ULTRASOUND DEVICES AND METHODS OF USE

(71) Applicant: University of Maryland, Baltimore, Baltimore, MD (US)

(72) Inventor: Steven P. Tropello, Baltimore, MD (US)

(73) Assignee: University of Maryland, Baltimore, Baltimore, MD (US)

(*) Notice: Subject to any disclaimer, the term of this patent is extended or adjusted under 35 U.S.C. 154(b) by 0 days.

(21) Appl. No.: 15/809,665

(22) Filed: Nov. 10, 2017

(65) Prior Publication Data

US 2018/0078234 A1 Mar. 22, 2018

Related U.S. Application Data

(63) Continuation of application No. 14/785,366, filed as application No. PCT/US2014/034950 on Apr. 22, 2014.
(Continued)

(51) Int. Cl.
*A61B 1/00* (2006.01)
*A61B 8/00* (2006.01)
(Continued)

(52) U.S. Cl.
CPC .......... *A61B 8/0841* (2013.01); *A61B 8/4209* (2013.01); *A61B 8/481* (2013.01);
(Continued)

(58) Field of Classification Search
CPC .............. A61J 15/0003; A61J 15/0088; A61M 25/0158; A61M 25/10; A61M 2025/0166;
(Continued)

(56) References Cited

U.S. PATENT DOCUMENTS 5,154,387 A 10/1992 Trailer
5,458,583 A 10/1995 McNeely et al.
(Continued)

FOREIGN PATENT DOCUMENTS

JP H6-503243 A 4/1994
JP H8-89583 A 4/1996
(Continued)

OTHER PUBLICATIONS

Office Action issued by the Japanese Patent Office for Application No. 2016-510734, dated Jan. 30, 2018, 12 pages (including 6 page English translation).
(Continued)

*Primary Examiner* — Peter Luong (57) ABSTRACT

Disclosed is a system and method for the placement of elongate medical members within a patient's body using coaptive ultrasound that combines magnetic guidance with ultrasound visualization of the medical member in the patient's body. A coaptive ultrasound probe adaptor magnetically attracts an elongate medical member within the patient with sufficient force so as to allow the operator to manually guide the member to its intended location. The adaptor mates with an ultrasound probe to provide the medical operator ultrasound feedback of the position of the member, thus allowing internal placement without the need for more specialized medical equipment.

6 Claims, 10 Drawing Sheets

Related U.S. Application Data (60) Provisional application No. 61/814,516, filed on Apr. 22, 2013.

(51) Int. Cl.

| | | |
|---|---|---|
| *A61B 8/08* | (2006.01) | |
| *A61M 25/01* | (2006.01) | |
| *A61J 15/00* | (2006.01) | |
| *A61B 1/01* | (2006.01) | |
| *A61M 25/10* | (2013.01) | |
| *A61B 17/00* | (2006.01) | |
| *A61B 17/34* | (2006.01) | |
| *A61B 90/00* | (2016.01) | |

(52) U.S. Cl.
CPC ....... *A61J 15/0003* (2013.01); *A61J 15/0088* (2015.05); *A61M 25/0158* (2013.01); *A61B 1/00158* (2013.01); *A61B 1/01* (2013.01); *A61B 2017/00876* (2013.01); *A61B 2017/3413* (2013.01); *A61B 2090/378* (2016.02); *A61M 25/10* (2013.01); *A61M 2025/0166* (2013.01); *A61M 2025/1079* (2013.01)

(58) Field of Classification Search
CPC ......... A61M 2025/1079; A61B 8/0841; A61B 8/4209; A61B 8/481; A61B 1/00158; A61B 1/01; A61B 2017/00876; A61B 2017/3413; A61B 2090/378
See application file for complete search history.

(56) References Cited

U.S. PATENT DOCUMENTS

| | | | |
|---|---|---|---|
| 5,681,260 A * | 10/1997 | Ueda | A61B 1/00082 128/899 |
| 6,015,414 A | 1/2000 | Werp et al. | |
| 6,126,647 A | 10/2000 | Posey et al. | |
| 6,173,199 B1 | 1/2001 | Gabriel | |
| 6,685,671 B1 | 2/2004 | Oishi et al. | |
| 6,702,804 B1 | 3/2004 | Ritter et al. | |
| 7,761,133 B2 | 7/2010 | Viswanathan et al. | |
| 7,769,428 B2 | 8/2010 | Viswanathan et al. | |
| 7,853,306 B2 | 12/2010 | Viswanathan et al. | |
| 7,963,910 B2 | 6/2011 | Okada | |
| 8,419,681 B2 | 4/2013 | Sell | |
| 8,677,990 B2 | 3/2014 | Gabriel | |
| 8,764,769 B1 | 7/2014 | Rodriguez-Navarro et al. | |
| 8,790,245 B2 | 7/2014 | Rodriguez Fernandez et al. | |
| 8,834,370 B2 | 9/2014 | Evert et al. | |
| 2006/0009735 A1 | 1/2006 | Viswanathan et al. | |
| 2006/0025675 A1 | 2/2006 | Viswanathan et al. | |
| 2006/0025676 A1 | 2/2006 | Viswanathan et al. | |
| 2006/0025719 A1 | 2/2006 | Viswanathan et al. | |
| 2006/0247530 A1 | 11/2006 | Hardin, Jr. et al. | |
| 2007/0205785 A1 * | 9/2007 | Nilsson | A61B 8/00 600/459 |
| 2008/0045863 A1 | 2/2008 | Bakos | |
| 2008/0294102 A1 | 11/2008 | Cartledge et al. | |
| 2009/0062772 A1 | 3/2009 | Wakeford et al. | |
| 2009/0198153 A1 | 8/2009 | Shriver | |
| 2010/0094116 A1 | 4/2010 | Silverstein | |
| 2010/0145147 A1 | 6/2010 | Pinsky et al. | |
| 2010/0179510 A1 | 7/2010 | Fox et al. | |
| 2012/0197062 A1 | 8/2012 | Requarth | |
| 2012/0265130 A1 | 10/2012 | De la Rama | |
| 2013/0072792 A1 | 3/2013 | Aggerholm et al. | |
| 2014/0039358 A1 | 2/2014 | Zhou et al. | |
| 2014/0180242 A1 * | 6/2014 | Tai | A61M 29/02 604/506 |
| 2014/0180252 A1 | 6/2014 | Gabriel | |
| 2014/0200504 A1 | 7/2014 | Roca-Singh | |
| 2014/0228680 A1 | 8/2014 | Fukuda | |
| 2014/0276941 A1 | 9/2014 | Rodriguez-Navarro et al. | |
| 2016/0081652 A1 | 3/2016 | Tropello | |
| 2016/0302811 A1 | 10/2016 | Rodriguez-Navarro et al. | |

FOREIGN PATENT DOCUMENTS

| | | |
|---|---|---|
| JP | H11-56852 A | 3/1999 |
| JP | 2003-93332 A | 4/2003 |
| JP | 2008-284136 A | 11/2008 |
| JP | 2012-501689 A | 1/2012 |
| JP | 2012-502749 | 2/2012 |
| JP | 2013-121390 | 6/2013 |
| WO | WO-99/36120 | 7/1999 |
| WO | WO-2006/005012 A2 | 1/2006 |
| WO | WO-2006/005012 A3 | 1/2006 |
| WO | WO 2010/033629 A1 | 3/2010 |
| WO | WO-2010/036721 A2 | 4/2010 |
| WO | WO-2010/036721 A3 | 4/2010 |
| WO | WO-2010/129327 A1 | 11/2010 |
| WO | WO 2012/003665 A1 | 1/2012 |
| WO | WO 2017/176881 A1 | 10/2017 |

OTHER PUBLICATIONS

International Search Report and Written Opinion issued by the International Examining Authority for Application No. PCT/US2014/034950, dated Oct. 1, 2014, 8 pages.

International Search Report and Written Opinion issued by the International Examining Authority for Application No. PCT/US2017/026141, dated Aug. 25, 2017, 11 pages.

Extended European Search Report issued by the European Patent Office for Application No. 14788472, dated Dec. 21, 2016, 7 pages.

Arias, Elizabeth, et al. "United States Life Tables, 2005." National Vital Stat Reports. vol. 58, No. 10. Mar. 2010.

Arora, Gaurav. Percutaneous Endoscopic Gastrostomy (PEG) Tube Placement. Dec. 27, 2012. Updated Dec. 14, 2015. http://emedicine.medscape.com/article/149665-overview#a01.

Duszak, Richard. "Percutaneous Gastrostomy and Jejunostomy." Dec. 27, 2012. Updated Jan. 14, 2014. http://emedicine.medscape.com/article/1821257-overview#aO 1.

Gauderer, Michael W. L. "Percutaneous endoscopic gastrostomy-20 years later: a historical perspective." Journal o Pediatric Surgery, 2001; 36: 217-219.

Lohsiriwat, Varul. "Percutaneous endoscopic gastrostomy tube replacement: A simple procedure?" World Journal of Gastrointestinal Endoscopy, Jan. 16, 2013; 5: 14-18.

Lynch, C.R. and J.C. Fang. "Prevention and Management of Complications of PEG tubes." Practical 3astroenterology, Nov. 2004; 66-76.

Rosenberg, Laura H., et al. "Late accidental dislodgement of a percutaneous endoscopic gastrostomy tube: an underestimated burden on patients and the health care system." Surgical Endoscopy, Oct. 2011; 25: 3307-3311.

Tsukuda, Toshinobu, et al. "Percutaneous Radiologic Gastrostomy Using Push-Type Gastrostomy Tubes with CT and Fluoroscopic Guidance." Interventional Radiology, Feb. 2006; 186: 574-576.

Office Action issued by the Japanese Patent Office for Application No. 2016-510734, dated Dec. 11, 2018, 10 pages (including 5 page English translation).

Extended European Search Report issued by the European Patent Office for Application No. 18177361.5, dated Jan. 23, 2019, 8 pages.

\* cited by examiner

COAPTATION ULTRASOUND DEVICES AND METHODS OF USE

CROSS-REFERENCE TO RELATED APPLICATIONS

This application is a continuation of U.S. patent application Ser. No. 14/785,366, filed Oct. 19, 2015, which claims priority under 35 U.S.C. § 371 to, and is a U.S. national phase entry of, International Application No. PCT/US2014/034950, filed Apr. 22, 2014, which is based upon and claims priority from U.S. Provisional Patent Application Ser. No. 61/814,516 entitled "Coaptation Ultrasound Devices and Methods of Use," filed with the United States Patent and Trademark Office on Apr. 22, 2013, the entire contents of each of which are herein incorporated by reference.

FIELD OF THE INVENTION

The present invention relates generally to placement of medical devices within a body in the medical field, and more particularly to methods and devices for ultrasound-guided placement of medical devices, such as catheters, conduits, carriers, electrodes, and the like into a patient's body.

BACKGROUND OF THE PRIOR ART

A wide variety of medical procedures require placement of medical devices at various locations within a patient's body. For instance, certain procedures may require the placement of electrodes within a patient's spine, or attachment of electrodes to heart tissue, or the like. In other procedures, medical staff may wish to place temperature probes or heating wires at various locations within patient's body. Further, for cancer treatment, medical staff may wish to place radioactive seeds or deliver therapeutic medications deep within a patient's body, including directly into internal organs. In still other procedures, medical staff may wish to place catheters or other fluid or material-carrying conduits within the patient's body for delivery of medications or other materials, for carrying forceps, biopsy instruments or the like into the patient's body, for providing suctioning to various parts of a patient's body, and many other procedures involving the placement of medical devices within the patient's body. Procedures for placing such medical devices vary widely from application to application, but all carry the common aspect of presenting challenge to the medical staff in manipulating such medical devices within the patient's body to route them to their intended location and position them for their intended use at that location.

More particularly, often times medical procedures require manipulation of a catheter or other conduit through portions of the patient's body that are not easily accessible, and thus make maneuvering of the conduit to its intended location quite challenging. For instance, it may be medically necessary to place conduits within internal body cavities to provide for the drainage of unwanted fluid, to provide for the infusion of medications into internal organs or elsewhere in the body, to provide for direct nutritional supplementation to patients unable to orally consume adequate nutrition, and the like. The procedures for guiding such conduits to their intended locations in a patient's body can be difficult to perform and can risk serious injury to the patient if not performed properly.

One such procedure that presents significant challenges is the placement of gastrostomy tubes for patients requiring direct nutritional supplementation into the stomach. Enteral feeding has been recommended when a patient has a functioning gut but is unable to eat for seven to fourteen days. When enteral feeding is anticipated to be required for longer than 30 days, a gastrostomy tube is preferred over a nasoenteric tube. The placement of gastronomy tubes has become a frequently required procedure, with more than 215,000 being placed annually in the United States. The vast majority of such procedures are performed by consultants, such as gastroenterologists and interventional radiologists, as opposed to an emergency room doctor, an intensivist, or patient's primary physician. This is because those specialized consultant physicians have access to and have been trained on the expensive equipment that one must use to safely enter (i.e., cannulate) the stomach (i.e., gastrostomy). This expensive equipment includes endoscopes, fluoroscopes, and computed tomography (CT) scanners, all of which require specialized training and skill to operate properly.

The most common method for initial gastrostomy tube insertion is Percutaneous Endoscopic Gastrostomy ("PEG"), involving placing of a PEG tube into the patient's stomach. When performing a typical PEG process, a patient is placed in the supine position. A nasal or oral gastric tube is then introduced into the patient's stomach. Gastric fluid is removed using suction, such as through fenestrations at the distal end of the nasal or oral gastric tube. The stomach is then insufflated by way of the gastric tube or an endoscope. In one method, the endoscope has a light at the distal end. When illuminated, the practitioner is supposed to identify a suitable puncture site that is free from interposed organs and large vessels by noting where the light from the endoscope shines through the abdominal skin of the patient. An incision is then made at the identified target site, and a sheathed needle is then entered into the insufflated stomach. A guide wire is then introduced through the abdominal sheath and into the stomach. A snare or forceps located at the distal end of the endoscope is manipulated to capture the end of the guide wire. The endoscope is then extracted, pulling the guide wire along and ultimately causing the guide wire to exit through the mouth or nose. Applicant is aware of two preferred methods to complete the gastrostomy after the guide wire has been routed from the outside of the patient's abdomen, into their stomach, up their esophagus and out through their mouth or nose: the Ponsky-Gauderer (pull-(on) string) method (the "PG method"), and the Sacks-Vine (push-over-wire) method (the "SV method").

If the PG method is selected, the gastrostomy tube is tied to the end of the guide wire that has exited through the patient's nose or mouth. The abdominal end of the guide wire is then pulled until the gastrostomy tube extends out from the hole in the abdomen, with the proximal end of the gastrostomy tube (having an enlarged end, or bumper, therein to prevent it from passing through the stomach wall and out of the patient's abdomen) remaining within and providing access to the interior of the patient's stomach. If the SV method is selected, the gastrostomy tube is placed over the guide wire and is pushed toward the stomach from the patient's mouth until it extends out from the abdominal hole. Again, the gastrostomy tube has a bumper to prevent the tube from passing entirely through the abdominal hole and causing the proximal end to remain in the stomach.

Alternatively, percutaneous gastrostomy placement can be performed using gastropexy methods. Gastropexy wires are inserted into the stomach via the angiocatheter and used to tether the stomach. Standard gastropexy techniques are then used to place the gastrostomy tube over a guide wire inserted only within the stomach.

Even with skilled consultant physicians handling these procedures, complications can occur including tube misplacement, inadvertent injury to surrounding tissues during placement, infections, tube clogging, and tube dislodgement during use. When such complications occur outside of the hospital, patients will often come to a hospital emergency room for help. However, as the PEG procedures require specialized skill in handling, emergency medicine physicians are often unable to perform the necessary procedures, and must instead call upon such specialist consultants, which adds to the overall expense and delay in treating the patient's issue, or risk of further complication or injury if someone lacking sufficient specialized skill attempts to address the issue.

Accordingly, there is a need in the art for a device and method that will allow for placement of a medical device into a patient's body, such as the performance of percutaneous gastrostomies, at the bedside and that will no longer require the expertise and equipment of specialist medical personnel, such as a gastroenterologist or other specialist. It would be advantageous to provide a method and device that would reduce the difficulties associated with installing medical devices inside of a patient's body, including medical instrument carriers, medication carriers, electrodes, probes, catheters and other conduits, and that would thereby reduce the risks of injury associated with previously known methods and devices.

DESCRIPTION OF THE INVENTION

Disclosed herein is a system and method for placement of a catheter, conduit, or other elongate member within a patient's body that utilizes coaptive ultrasound that combines magnetic guidance with ultrasound visualization of the elongate member in the patient's body. Such system and method are suitable for use in therapeutic interventional and/or diagnostic procedures, and may be useful for placement and guiding of medical devices, including catheters or other conduits, in varied tissue planes and cavities in a patient's body, including by way of non-limiting example the thorax, abdomen, blood vessels, and pericardium, for diagnostic, therapeutic, and/or procedural purposes. For example, such system and method may be useful in the placement and manipulation of a catheter within a patient's stomach during a procedure for placement of a gastrostomy tube. Further, such system and method may be useful in the positioning and manipulation of a suction tube within a patient's body to remove unwanted fluid, such as by way of an initial surgical insertion of the suction tube in a region within the patient's body that has a low risk of complication or injury, and then fine manipulation of the suction tube in the intended location through magnetic guidance from outside of the patient's body. Similarly, such system and method may be useful for delivering medications through a conduit to targeted regions or organs within the patient's body, and for deploying probes, sensors, electrodes, and similarly configured devices within the patient's body. Still further, such system and method may be useful in obtaining tissue, fluid, and biopsy samples from within the patient's body, such as by magnetically guiding a forcep- or biopsy instrument-carrier to the intended site within the patient's body.

As used herein, all of such carriers, catheters, conduits, delivery devices, internal probes and sensors, electrodes, and the like that are intended for insertion into and movement or manipulation within a patient's body are referred to generally as "elongate medical members."

A coaptive ultrasound probe adaptor is provided that is configured to magnetically attract an elongate medical member, such as a catheter or the like, positioned within the patient with sufficient force so as to allow the medical operator to manually guide the catheter or other conduit or elongate medical member to its intended location. The adaptor is also configured to mate with an ultrasound probe, such that as the medical operator is remotely manipulating the catheter or other elongate medical member, they may likewise receive visual ultrasound feedback of the position of the catheter or other elongate medical member within the patient's body. By allowing visual confirmation through the use of readily-available ultrasound equipment, internal catheter, conduit, or other elongate medical member placement can be achieved without the need for expensive, specialized equipment, such as endoscopes, fluoroscopes, and CT scanners. Thus, the system and method disclosed herein will enable acute care physicians, such as emergency medicine physicians and critical care physicians (i.e., intensivists), or other healthcare providers trained in the art of ultrasound, to place such catheters, conduits, and other elongate medical members safely and reliably.

With regard to certain aspects of an embodiment of the invention, the system and method may be used for inserting gastrostomy tubes in a simple bedside procedure without requiring the use of specialized consultants or specialized equipment including endoscopes, fluoroscopes, and CT scanners. The system and method make use of more widely available medical devices that require less specialized training to use, such as ultrasounds, feeding tubes, guide wires, and dilators. By allowing a wider population of medical operators to perform such procedures, the system and method disclosed herein offer safer, more immediate and more cost-effective care. For example, unlike endoscopes, ultrasound ensures that an adequate window for percutaneous gastrostomy tube insertion is present by providing visual confirmation that no bowel, organs, or blood vessels obstruct the cannulation track between the skin surface and the stomach wall. Further, with this procedure, emergency medicine physicians may easily re-insert dislodged gastrostomy tubes and immediately discharge patients back to their residence instead of admitting them for traditional PEG placement to be performed by a specialist consultant, thus saving time and decreasing consultation costs, hospital admission costs, patients' stress, and the risk of nosocomial infection. Geriatricians and rehabilitation physicians may likewise use the system and method disclosed herein in nursing home and rehabilitation facilities. This practice could dramatically reduce overall costs by eliminating transportation costs and thus avoiding all hospital fees.

Still other applications of the disclosed system and method for magnetically attracting an internally positioned elongate medical member to an externally positioned, ultrasound-enabled adapter for coordinated movement and manipulation of the elongate medical member by the adapter will be apparent to those of ordinary skill in the art without departing from the spirit and scope of the invention.

With regard to further aspects of an embodiment of the invention, a kit embodying the system is provided that may also include feeding tubes, guide wires, and dilators.

BRIEF DESCRIPTION OF THE DRAWINGS

The numerous advantages of the present invention may be better understood by those skilled in the art by reference to the accompanying figures in which.

BEST MODE(S) FOR CARRYING OUT THE INVENTION

The invention summarized above may be better understood by referring to the following description, claims, and accompanying drawings. This description of an embodiment, set out below to enable one to practice an implementation of the invention, is not intended to limit the preferred embodiment, but to serve as a particular example thereof. Those skilled in the art should appreciate that they may readily use the conception and specific embodiments disclosed as a basis for modifying or designing other methods and systems for carrying out the same purposes of the present invention. Those skilled in the art should also realize that such equivalent assemblies do not depart from the spirit and scope of the invention in its broadest form.

Figure 1:
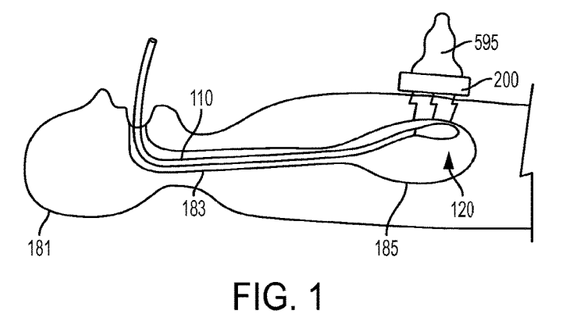
FIG. 1 is a schematic view of a gastric tube and ultrasound probe adaptor used for gastrostomy procedures in accordance with certain aspects of an exemplary embodiment of the invention.

FIG. 1 is a schematic view of a system in accordance with certain aspects of an exemplary embodiment of the invention. As shown in FIG. 1, a gastric tube 110 is inserted into a patient's stomach 185, entering the patient through the head 181 (either through the patient's mouth or nose) and down through the patient's esophagus 183, with the distal end (shown generally at 120) of gastric tube 110 ultimately being positioned within the patient's stomach. Also as shown in FIG. 1, an ultrasound probe adaptor 200, which is configured to receive an ultrasound probe 595, is positionable on the outside of the patient's abdomen, and may be manually moved by a medical operator, along with ultrasound probe 595, to provide a visual image of the patient's abdomen using ultrasound methods well known to those of ordinary skill in the art.

Ultrasound probe adaptor 200 and the distal end of gastric tube 110 are configured to be magnetically attracted to each other. More particularly, both ultrasound probe adaptor 200 and the distal end of gastric tube 110 (or other elongate medical member, such as a catheter or conduit member as may be used throughout a patient's body and particularly other than in a patient's stomach) have magnetic members, as will be discussed in further detail below, that provide a sufficient attraction force between them so as to (i) cause the distal end of gastric tube 110 to come into contact with the internal tissue surface that is immediately adjacent the distal end of gastric tube 110 and closest to probe adaptor 200, and (ii) cause distal end of gastric tube 110 to move within the patient's body in response to movement of probe adaptor 200 and in a motion that corresponds to motion of probe adaptor 200 outside of the patient's body. While the particular magnetic members necessary to provide such magnetic attraction may vary, specific configurations of such magnetic members will be described by way of example in further detail below.

Figure 2:
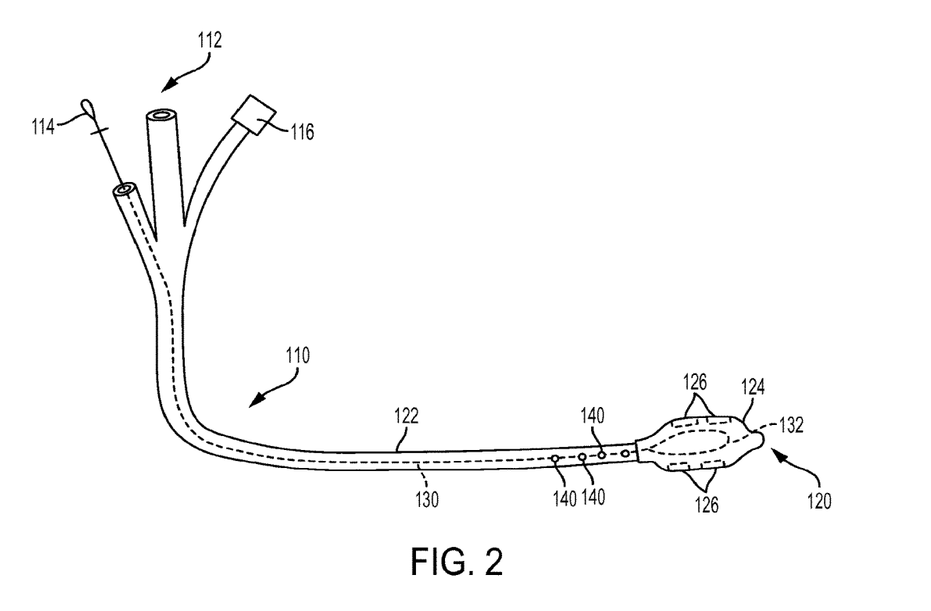
FIG. 2 is a side view of the gastric tube of FIG. 1.

As shown in the detail view of FIG. 2 and in accordance with certain features of an exemplary embodiment, gastric tube 110 comprises a lumen 122 extending from proximal end 112 of gastric tube 110 to distal end 120 of gastric tube 110. Proximal end 112 of gastric tube 110 may be provided additional functional elements, including a snare release 114, which provides a mechanism allowing the practitioner to control a snare positioned at distal end 132. The practitioner may push or pull snare release 114 to open or close the snare 132. Further, a syringe port 116 may be provided at proximal end 112 of gastric tube 110, providing a passageway to inflate a balloon 124 at the distal end 120 of gastric tube 110. Further, in some embodiments of the invention, one or more ports (not shown) may be provided at proximal end 112 of gastric tube 110 to connect external suction or insufflation devices. Such suction and insufflation ports may connect to one or more lumens that extend along the length of gastric tube 110.

With continued reference to FIG. 2, distal end 120 of gastric tube 110 includes one or more balloons 124 that may be inflated by the practitioner, such as by injecting a fluid through syringe port 116 into balloon 124 via lumen 122. Inflation of the balloon 124 inside of the patient's stomach 185 will provide an echogenic space that may be observed by the practitioner when viewing an ultrasound image of the patient's stomach produced by ultrasound probe 595, thus allowing the practitioner to confirm that the distal end 120 of gastric tube 110 is in its intended location within the patient's body.

Those skilled in the art will recognize that while a balloon 124 is shown as providing an echogenic space that may be observed via ultrasound, other echogenic configurations that will provide an image through an ultrasound procedure may likewise be provided on an elongate medical member without departing from the spirit and scope of the invention.

In order to configure distal end 120 so as to be magnetically attracted to ultrasound probe adaptor 200, distal end 120 is also preferably configured with one or more magnets 126. For example, magnets 126 may be positioned within and fixedly attached to the interior walls of balloon 124. Alternatively or additionally, magnets 126 may be located along the shaft of distal end 120 of gastric tube 110, and may be positioned internally along the distal end 120 of gastric tube 110, or externally (such as by clipping, by adhesive attachment, or otherwise) along the distal end 120 of gastric tube 110 or on the outside of balloon 124, without departing from the spirit and scope of the invention. Many different configurations of magnets 126 may be used in order to ensure proper alignment with and attraction to ultrasound adaptor 200.

Still further, distal end 120 of gastric tube 110 may be provided one or more tube fenestrations 140 that communicate with suction and/or insufflation ports at proximal end 112 of gastric tube 110, if such ports are provided. Likewise, snare 132 is located at distal end 120 of gastric tube 110, which snare 132 communicates with a snare operator, such as snare release 114, via snare line 130.

Figure 3:
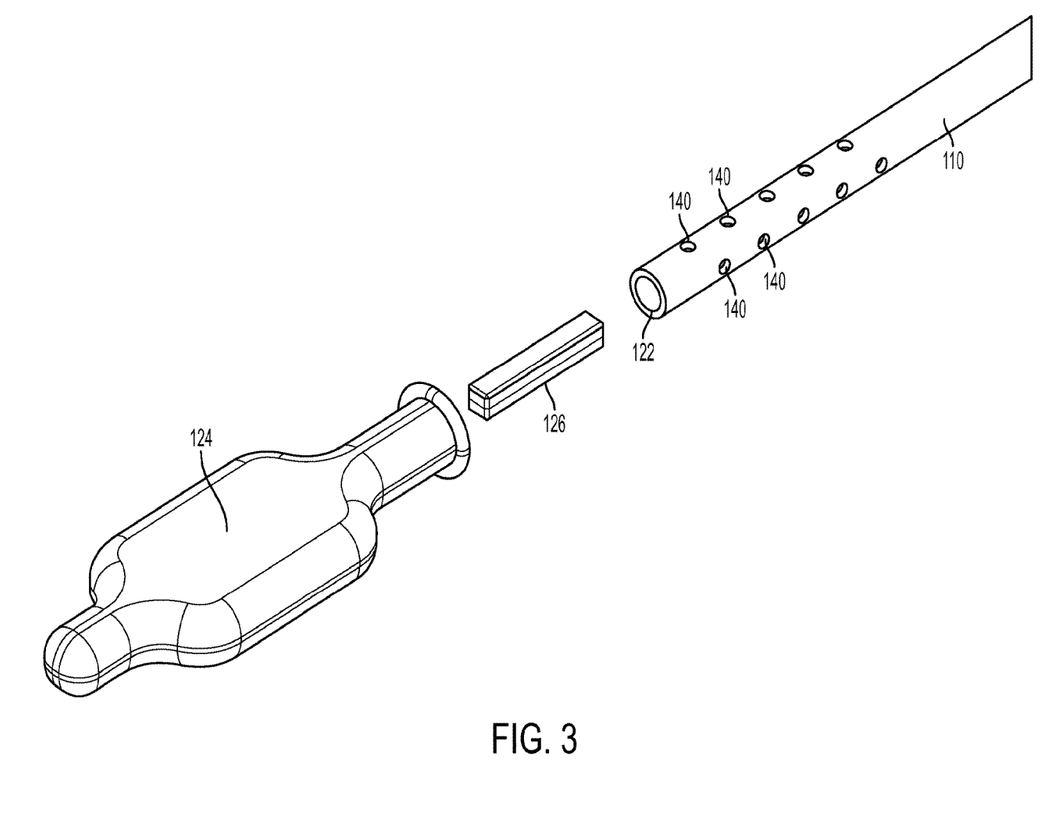
FIG. 3 is a close-up perspective exploded view of the distal end of the gastric tube of FIG. 1.

FIG. 3 shows a close-up exploded view of distal end 120 of gastric tube 110 according to certain aspects of an exemplary embodiment of the invention. As shown in FIG. 3, gastric tube 110 may be a generally cylindrical tube, and fenestrations 140 may be provided at the end of gastric tube 110 and aligned in axially-extending rows around the circumference of the end of gastric tube 110. Lumen 122 extends through gastric tube 110. Likewise, a flexible, inflatable balloon, which may be formed in varying shapes and sizes, is affixed to the end of gastric tube 110 and is in fluid communication with lumen 122 so that it may be inflated from the proximal end of gastric tube 110 with an echogenic medium, contrast agent or therapeutic agent. One or more magnets 126, such as by way of non-limiting example a neodymium block magnet having an approximate thickness of ¼" and an approximate length of 1½", is also situated in the distal end 120 of gastric tube 110, and may be positioned within balloon 124, within lumen 122, or bridging a portion of both balloon 124 and lumen 122. Further, magnet 126 may be rigidly affixed to balloon 124 and/or lumen 122, or may alternatively be positioned therein without fixation, so long as magnet 126's position will cause balloon 124 to be magnetically drawn toward ultrasound probe adaptor 200 when the probe adaptor is placed against the patient's abdomen. In a most preferred configuration, magnets 126 are situated along opposite side edges of balloon 124 so as to allow them to align with magnets positioned on ultrasound adaptor 200, as further detailed below. Snare 132 and snare line 130 are not shown in FIG. 3 for clarity, but those skilled in the art will recognize that such elements would be present and in a configuration as is well known in the art.

Figure 4:
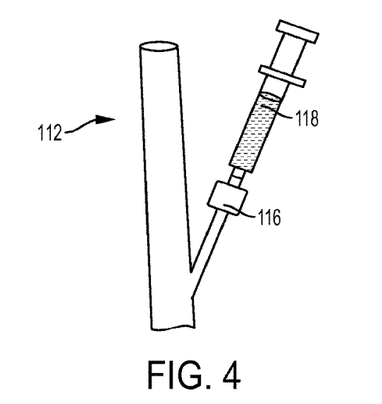
FIG. 4 is a close-up side view of the proximal end of the gastric tube of FIG. 1.

FIG. 4 provides a close-up view of syringe port 116 located at the proximal end of gastric tube 110. In the illustrated embodiment, syringe port 116 is attached to a syringe 118. Syringe 118 may be filled with any type of fluid that is capable of expanding balloon 124 with an echogenic medium, contrast agent or therapeutic agent. In preferred embodiments, syringe 118 is filled with a non-toxic fluid that will enhance ultrasound imaging, such as by way of non-limiting example, water or saline. Gases may also be used to inflate balloon 124. While the illustrated embodiment shows syringe 118 being a removable element, in certain embodiments syringe 118 may be a permanent element, making the fluid transfer system between syringe 118 and balloon 124 a closed system.

Figure 5A:
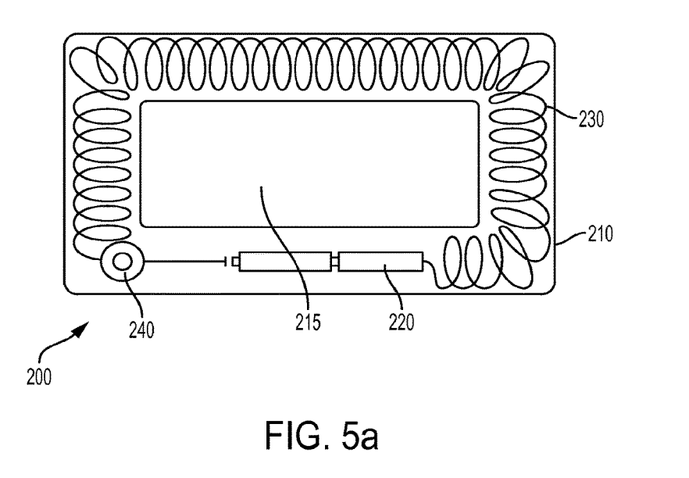
FIG. 5a is a schematic, cross-sectional top-down view of the ultrasound probe adaptor of FIG. 1.

Next, FIG. 5a shows a schematic, cross-sectional top-down view of a coaptive ultrasound probe adaptor 200 in accordance with certain aspects of an embodiment of the invention. Adaptor 200 may be formed in a variety of different shapes to receive existing or yet-to-be-developed ultrasound probes. As used herein, "ultrasound probe" is intended to refer to any hand-held device configured to provide ultrasound imaging. Ultrasound probe adaptor 200 includes a magnetic source, and is physically configured so as to attach to an ultrasound probe 595. In the embodiment shown in FIG. 5a, the magnetic source comprises an electromagnet having a power source 220, a variable resistor dial 240, and a coil 230, all contained within an external housing 210. Likewise, in order to attach to an ultrasound probe in the illustrated embodiment of FIG. 5a, housing 210 is provided an ultrasound probe receiver, such as a central cavity 215, into which the scanning head of an ultrasound probe may be inserted. Alternatively, adaptor 200 may attach to an ultrasound probe 595 by clipping on to one or more edges of the probe, or in other ways as may be apparent to those of ordinary skill in the art. Likewise, while the illustrated embodiment of FIG. 5a depicts a single electromagnetic configuration, other magnetic configurations and types may be used, such as ferromagnets positioned within housing 210, without departing from the spirit and scope of the invention. Likewise, variable resistor dial 240 or other adjustment devices may be used to increase or decrease the magnetic force of coil 230, in static or alternating frequency patterns, or alternatively no adjustment device may be provided, again without departing from the spirit and scope of the invention.

Figure 5B:
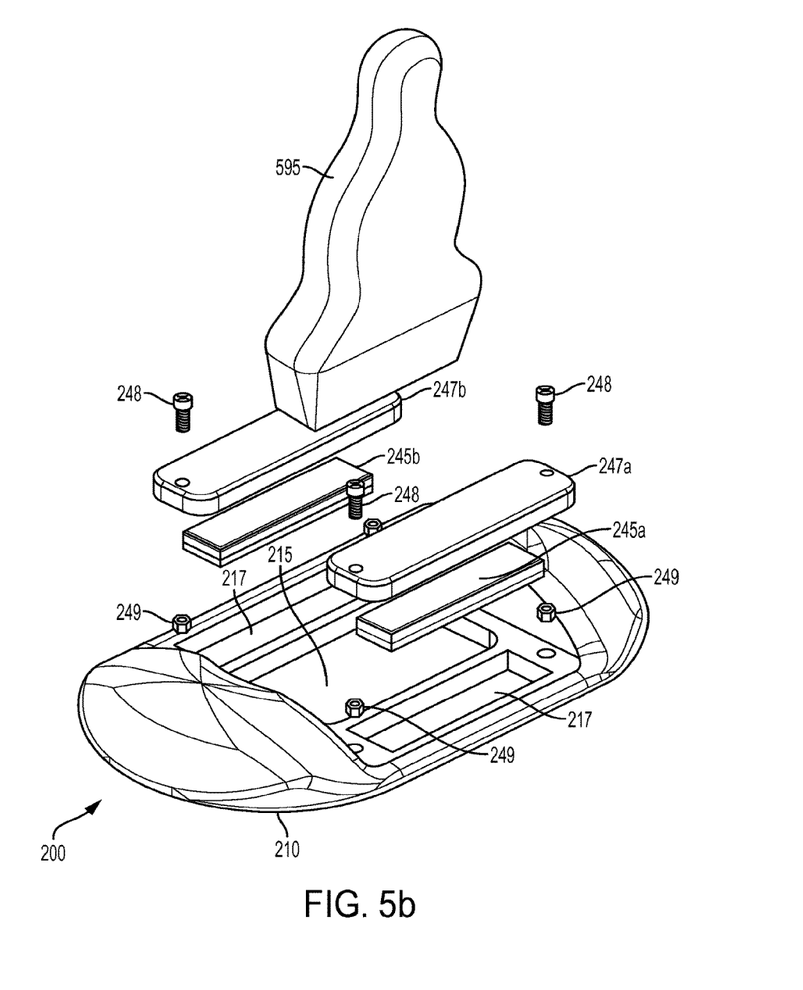
FIG. 5b is a perspective exploded view of an ultrasound probe adaptor in accordance with certain aspects of an embodiment of the invention.

FIG. 5b shows a close-up exploded view of a coaptive ultrasound probe adaptor 200, along with an ultrasound probe 595, according to certain aspects of a particularly preferred embodiment of the invention. As shown in FIG. 5b, ultrasound probe adaptor 200 includes base 210 having central cavity or opening 215 centrally located in the base 210 and extending through the entire thickness of base 210, such that ultrasound probe 595 may be placed in opening 215 and in contact with a patient's skin on which ultrasound probe adaptor 200 is positioned. With regard to an aspect of a particularly preferred embodiment of the invention, opening 215 is sized having a width dimension that is less that the width of balloon 124 on gastric tube 110, such that the sides of the balloon 124 extend past the long side edges of opening 215 when balloon 124 is magnetically attracted to ultrasound probe adaptor 200. Further, magnet receiving slots 217 are positioned at opposing sides of opening 215, and are each configured to removably receive a magnet 245a and 245b therein. Preferably, the magnets 245a and 245b are situated in opposite orientations from one another within their respective slots in ultrasound probe adaptor 200. As a result, the practitioner is assured that ultrasound probe adaptor 200 will magnetically attract a balloon 124, regardless of the orientation of the balloon 124 within the patient's body (i.e., regardless of which magnet pole is facing towards ultrasound probe adaptor 200). In one embodiment, ultrasound probe adaptor 200 is configured to position magnets 245a and 245b a distance away from one another that approximately matches the distance between magnets 126 positioned in balloon 124 so as to provide for alignment of the long axes of balloon 124 and ultrasound probe adaptor 200 when the two are magnetically attracted to one another. A first cover plate 247a may cover the magnet receiving slot 217 that receives magnet 245a, and a second cover plate 247b may cover the magnet receiving slot 217 that receives magnet 245b. Each such cover plate 247a and 247b is preferably removably held over its designated receiving slot 217 with removable connectors, such as threaded bolts 248 that extend into nuts 249 that in turn are held within base 110. As cover plates 247a and 247b are removable, and as magnets 245a and 245b are removable from slots 217, magnets of varying strength may be positioned within slots 217 so as to vary the amount of magnetic attraction that will be realized between ultrasound probe adaptor 200 and balloon 124, which may be necessary for varying medical procedures and varying patient physiology (i.e., with larger tissue planes between the ultrasound probe adaptor 200 and balloon 124 requiring larger magnetic attraction and in some cases repulsion).

Figure 6:
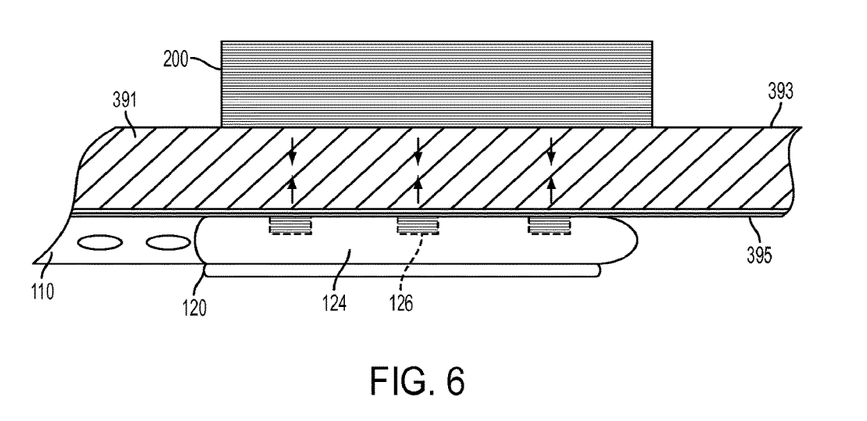
FIG. 6 is a side, cross-sectional view a patient's abdomen showing the positioning of an ultrasound probe adaptor in relation to the distal end of a gastric tube of FIG. 1.
Figure 7:
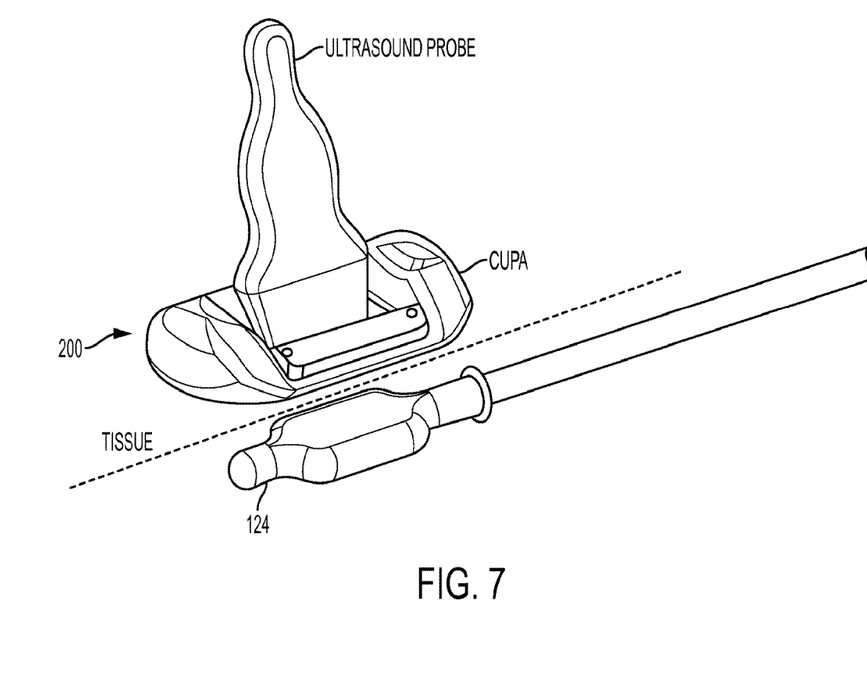
FIG. 7 is a side perspective view of the positioning of an ultrasound probe adaptor in relation to the distal end of a gastric tube of FIG. 1 in accordance with certain aspects of an exemplary embodiment of the invention.

Next, FIG. 6 shows a cross-sectional view and FIG. 7 a perspective view of the coaptive ultrasound probe adaptor 200 interacting with balloon 124 through a tissue plane. More particularly, the distal end 120 of gastric tube 110 having balloon 124 is shown in FIG. 6 positioned inside of a patient's stomach, with ultrasound probe adaptor 200 positioned outside of the patient's body and in contact with the skin of the patient's abdomen. In the illustrated embodiment, ultrasound probe adaptor 200 is positioned directly against the patient's skin 393, and the magnetic forces that attract balloon 124 to ultrasound probe adaptor 200 extend through the patient's skin 393, through the subcutaneous tissue 391, and through the stomach wall 395 (such tissue planes being hidden in FIG. 7 for clarity). Magnetic members in each of ultrasound probe adaptor 200 and balloon 124, such as magnets 126, cause balloon 124 to come into contact with stomach wall 395 and to push stomach wall 395 against the subcutaneous tissue 391 of the patient's abdomen (defined as coaptation), thus easing access to balloon 124 with a needle, cannula, or other device as described in greater detail below. Moreover, as best seen in FIG. 7, the position of magnets 126 in balloon 124 and of magnets 245a and 245b in ultrasound probe adaptor 200 may cause the balloon 124 and adaptor 200 to align their long axes with one another, and allow coordinated movement between the two.

Figure 8:
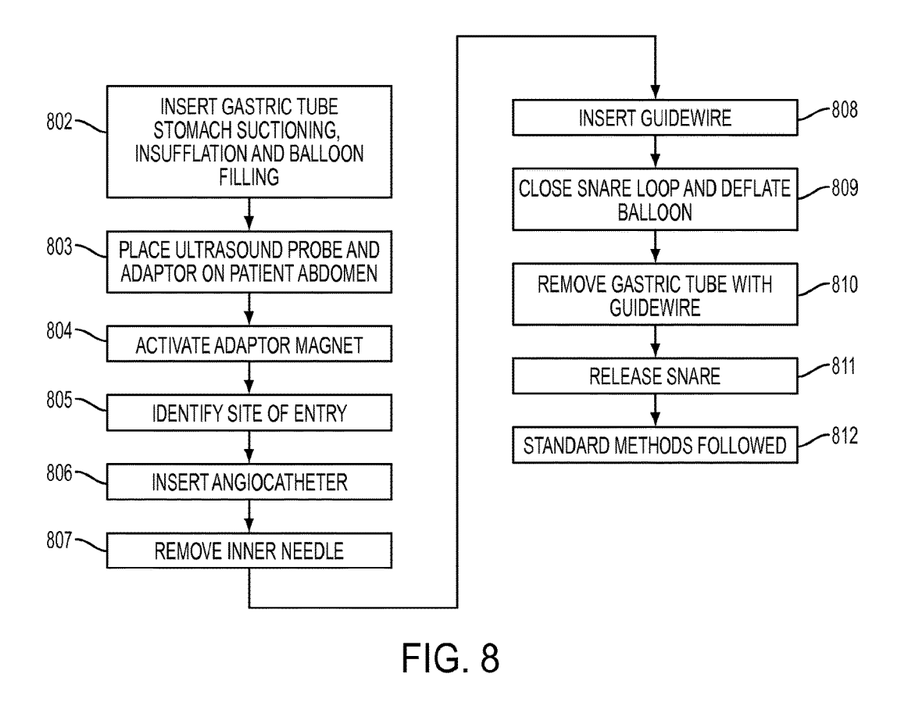
FIG. 8 is a flow diagram schematically representing an exemplary method of performing a gastrostomy in accordance with certain aspects of an embodiment of the invention.

FIG. 8 is a flow diagram that depicts one method of performing a gastrostomy using the system of the present invention. Although steps are depicted in FIG. 8 as integral steps in a particular order for purposes of illustration, in other embodiments, one or more steps, or portions thereof, are performed in a different order, or overlapping in time, in series or in parallel, or are omitted, or one or more additional steps are added, or the method is changed in some combination of ways. Some of the steps are illustrated in FIGS. 9 through 12. Moreover, while such method steps are specifically recited as corresponding to the performance of a gastrostomy, such gastrostomy process is referenced as exemplary only, and those of ordinary skill in the art will recognize that such method may be readily modified for many other procedures benefitting from remote, magnetic manipulation of an elongate medical member under ultrasound guidance using the general coaptive ultrasound methods shown in FIG. 8 without departing from the spirit and scope of the invention.

Figure 9:
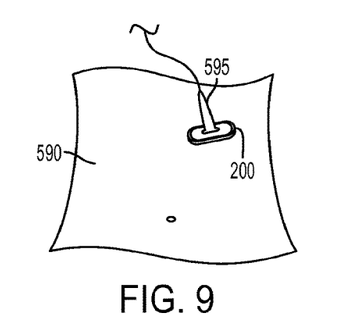
FIG. 9 is a schematic view of the placement of an ultrasound probe on a patient's body.

First, in step 802, a gastric tube 110 configured as above is inserted through a patient's nose or mouth until the distal end 120 of the gastric tube 110 is positioned inside of the patient's stomach. Existing stomach contents are extracted, for example by applying suction through fenestrations 140 in the gastric tube 110. Next, the stomach is insufflated, for example by using both the same or different channels and fenestrations in the gastric tube 110. Syringe 118 is filled with non-toxic fluid. In steps 803 and 804, ultrasound probe 595 and adaptor 200 are placed on the patient's abdomen 590 (as shown in FIG. 9). If the ultrasound probe adaptor is provided an electromagnet, it is activated at this time. As a result of the magnetic attraction between the ultrasound probe adaptor 200 and the distal end of gastric tube 120, the two components will align with one another along their long axes. Next, a suitable entry point is identified in step 805. Ultrasound probe 595 is used to ultrasonically image the patient's internal abdomen to detect any interposed organs or large vessels positioned between the ultrasound probe adaptor 200 and the balloon 124.

In the event that ultrasound probe adaptor 200 is provided an electromagnet assembly, the strength of the magnet may be adjusted using the variable resistor dial 240. Likewise, if ferromagnets are positioned in ultrasound probe adaptor 200, the strength of the magnetic force generated by ultrasound probe adaptor 200 may be modified by simply changing the magnets 245a and 245b in adaptor 200. In some cases, it may be necessary to reduce the magnetic attraction to allow for coordinated movement of the devices until a suitable entry point is identified. In other instances, it may be necessary to increase the magnetic attraction to account for excessive subcutaneous tissue. In any case, once a proper entry point is identified, the depth of the subcutaneous tissue may be measured to give the practitioner a reference point before making an incision.

Figure 10:
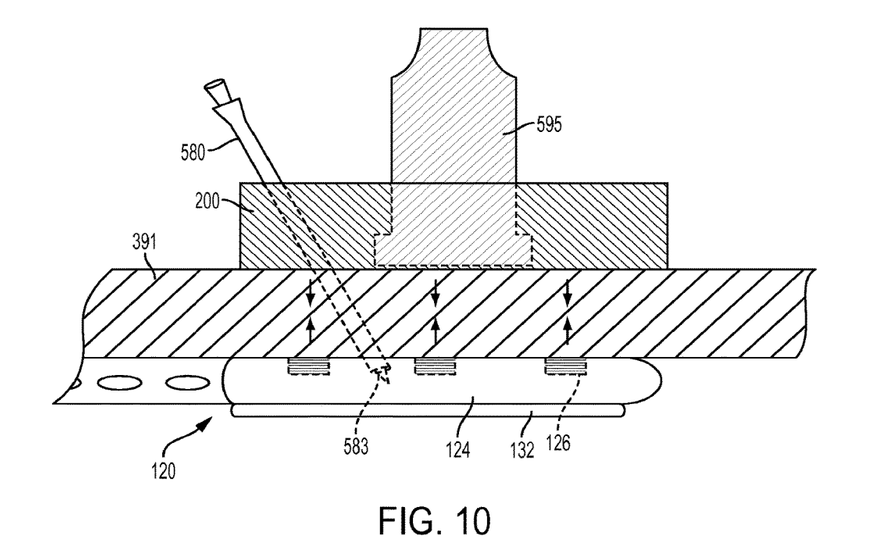
FIG. 10 is a schematic view of the insertion of an angiocatheter into a patient's stomach in accordance with certain aspects of an embodiment of the invention.
Figure 11:
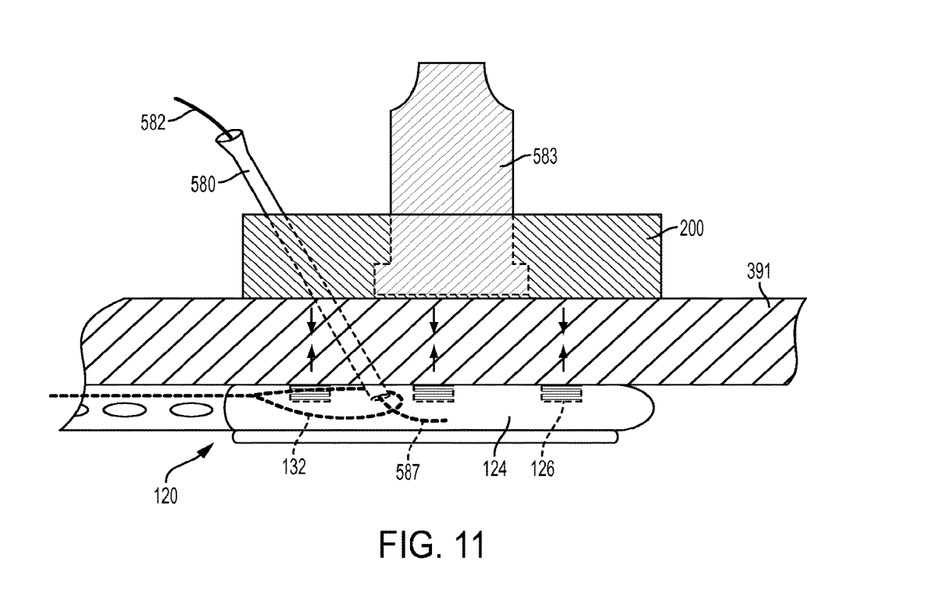
FIG. 11 is a schematic view of the capture of a guide wire within a patient's stomach in accordance with certain aspects of an embodiment of the invention.
Figure 12:
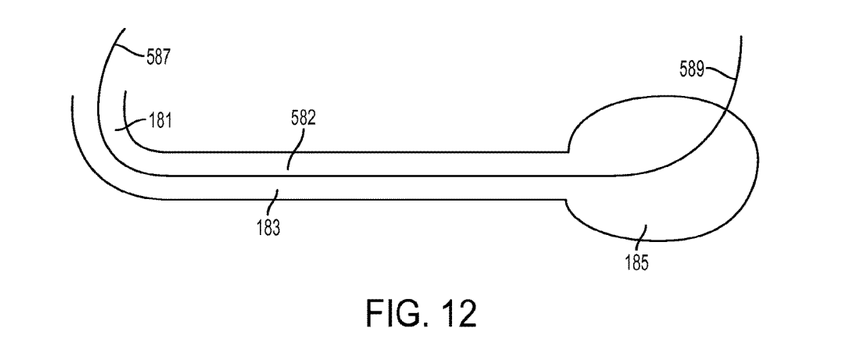
FIG. 12 is a schematic view of a guide wire placed within a patient's body in accordance with certain aspects of an embodiment of the invention.

Next, in step 806, and as shown in FIG. 10, an inner needle 583 and angiocatheter 580 are inserted into the patient's stomach through the abdomen, preferably through opening 215 in adaptor 200 Inner needle 583 is then removed in step 807, and in step 808 (and as shown in FIG. 11), guide wire 582 is introduced through angiocatheter 580. Once the distal end 587 of guide wire 582 is fed through snare 132, snare 132 is closed and the balloon 124 is deflated in step 809. Next, gastric tube 110 is removed from the patient in step 810, and snare 132 is released in step 811 when the gastric tube is completely removed. FIG. 12 shows the final result of the method, in which guide wire 582 extends from the patient's stomach 185, through the esophagus 183, and out through the patient's head 181. The proximal end 589 terminates outside of the patient's stomach. The distal end 587 terminates outside of the patient's nose or mouth. Once guide wire 582 is in place, the feeding tube may be inserted at step 812 using either the Ponsky-Gauderer method or the Sacks-Vine method, as described above.

In another embodiment, the devices of the present invention are used to introduce a percutaneous gastrostomy tube into a patient using gastropexy methods. In this method, steps 802 through 807 remain the same. However, after the inner needle is removed, one or more gastropexy anchors are inserted into the patient's stomach. Once the one or more anchors are fixated, standard gastrostomy methods follow using a guide wire placed only within the stomach.

Figure 13:
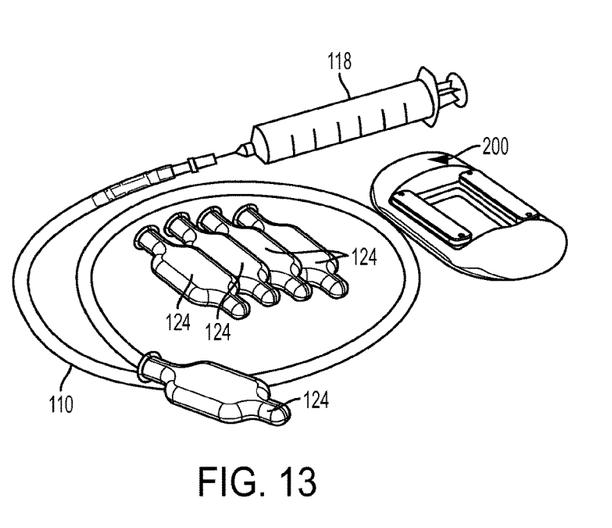
FIG. 13 shows a kit for placing a conduit within a patient's body in accordance with certain aspects of an embodiment of the invention.

FIG. 13 shows a kit for placing an elongate medical member, such as a conduit, within a patient's body in accordance with certain aspects of an embodiment of the invention. As shown in FIG. 13, a kit preferably includes at least an ultrasound probe adaptor 200 configured as described above, a conduit 110, a syringe 118 for connection to a proximal end of conduit 110, a plurality of inflatable balloons 124 for connection to the distal end of conduit 110, and at least one magnet 126 sized for insertion into each of balloons 124. Preferably, more than one magnet 126 is provided, with the magnets preferably having differing magnetic strengths that a practitioner may select for a particular circumstance (e.g., for tissue planes of varying thickness). Also, while not shown in FIG. 13, additional elements could be provided with such a kit, including items such as feeding tubes or other supply or fluid drainage conduits, guide wires, dilators, and the like, all without departing from the spirit and scope of the instant invention.

In the foregoing specification, the invention has been described with reference to specific embodiments thereof. It will, however, be evident that various modifications and changes may be made thereto without departing from the broader spirit and scope of the invention. The specification and drawings are, accordingly, to be regarded in an illustrative rather than a restrictive sense. Throughout this specification and the claims, unless the context requires otherwise, the word "comprise" and its variations, such as "comprises" and "comprising," will be understood to imply the inclusion of a stated item, element or step or group of items, elements or steps but not the exclusion of any other item, element or step or group of items, elements or steps. Furthermore, the indefinite article "a" or "an" is meant to indicate one or more of the item, element or step modified by the article.

Having now fully set forth the preferred embodiments and certain modifications of the concepts underlying the present invention, various other embodiments as well as certain variations and modifications of the embodiments herein shown and described will obviously occur to those skilled in the art upon becoming familiar with said underlying concepts. It should be understood, therefore, that the invention may be practiced otherwise than as specifically set forth herein.

INDUSTRIAL APPLICABILITY

The present invention is applicable to devices and methods for placing medical devices into and manipulating such medical devices within patients, particularly through ultrasound-guided placement and manipulation. The devices can be made in industry and practiced in the medical device field.

The invention claimed is:

1. A method comprising:
   inserting a distal end of a tube into a stomach of a patient via the patient's esophagus, the distal end of the tube having a balloon and a magnet coupled thereto;
   expanding the balloon such that the balloon defines an ultrasound echogenic interior volume;
   applying an external magnetic source to a skin of the patient;
   moving the external magnetic source along the skin of the patient to move the balloon within the stomach of the patient via a magnetic attraction between the external magnetic source and the magnet and to maintain the balloon in contact with a wall of the stomach via the magnetic attraction between the external magnetic source and the magnet;
   using an ultrasound probe applied to the skin of the patient, visualizing the balloon and the patient's internal abdomen to detect any organs or large blood vessels interposed between the ultrasound probe and the balloon;
   inserting a needle through the skin of the patient, through a stomach wall of the patient, through the balloon and into the interior volume;
   inserting a distal end of a guidewire through the needle and into the interior volume;
   retaining the distal end of the guidewire in the interior volume; and
   withdrawing the distal end of the guidewire from the patient by withdrawing the tube and the balloon from the patient via the patient's esophagus.

2. The method of claim 1, further comprising adjusting a position of the balloon via movement of the external magnetic source if interposed organs and large vessels are visualized between the balloon and the skin of the patient by the ultrasound probe.

3. The method of claim 1, wherein, during the visualizing, the ultrasound probe is applied to the skin such that the ultrasound probe is adjacent to the external magnetic source.

4. The method of claim 1, wherein the external magnetic source is coupled to an ultrasound probe adapter having an opening therethrough, further comprising disposing the ultrasound probe through the opening.

5. The method of claim 1, wherein expanding the balloon includes expanding the balloon within the stomach.

6. The method of claim 1, wherein visualizing the balloon and the patient's internal abdomen includes generating an image of the balloon and visualizing a position of the balloon within the patient.

* * * * *